US012742144B2

(12) United States Patent
Schutte et al.

(10) Patent No.: US 12,742,144 B2
(45) Date of Patent: Sep. 22, 2026

(54) SYSTEMS, DEVICES AND METHODS FOR ENGINEERED TISSUE CONSTRUCT TRANSPORT AND CONTAINMENT

(71) Applicant: Humacyte Global, Inc., Durham, NC (US)

(72) Inventors: Robert Schutte, Cary, NC (US); Dustin Cashman, Chapel Hill, NC (US); Heather L. Prichard, Wake Forest, NC (US); Joshua Mccall, Seattle, WA (US); William E. Tente, Seekonk, MA (US); Shannon L.M. Dahl, Palo Alto, CA (US); Laura E. Niklason, Greenwich, CT (US)

(73) Assignee: Humacyte Global, Inc., Durham, NC (US)

(*) Notice: Subject to any disclaimer, the term of this patent is extended or adjusted under 35 U.S.C. 154(b) by 974 days.

(21) Appl. No.: 17/784,928

(22) PCT Filed: Dec. 11, 2020

(86) PCT No.: PCT/US2020/064598
§ 371 (c)(1),
(2) Date: Jun. 13, 2022

(87) PCT Pub. No.: WO2021/119486
PCT Pub. Date: Jun. 17, 2021

(65) Prior Publication Data

US 2023/0026520 A1 Jan. 26, 2023

Related U.S. Application Data

(60) Provisional application No. 62/946,645, filed on Dec. 11, 2019.

(51) Int. Cl.
*C12M 1/00* (2006.01)
*C12M 1/12* (2006.01)
*C12M 3/00* (2006.01)

(52) U.S. Cl.
CPC .............. *C12M 45/22* (2013.01); *C12M 1/12* (2013.01); *C12M 21/08* (2013.01); *C12M 37/04* (2013.01)

(58) Field of Classification Search
None
See application file for complete search history.

(56) References Cited

U.S. PATENT DOCUMENTS 4,597,765 A * 7/1986 Klatt .................... A61F 2/0095 600/40
5,964,261 A * 10/1999 Neuenfeldt .......... A61K 9/0024 206/439

(Continued)

FOREIGN PATENT DOCUMENTS

WO WO-0108630 A2 * 2/2001 ............. A01N 1/146
WO WO-2021119486 A1 6/2021

OTHER PUBLICATIONS

Lawson et al. "Bioengineered human acellular vessels for dialysis access in patients with end-stage renal disease: two phase 2 single-arm trials." Lancet 2016; 387: 2026-34. (Year: 2016).*

(Continued)

*Primary Examiner* — William H. Beisner

(57) ABSTRACT

In some embodiments, an engineered tissue construct (ETC) transport and containment method is provided and includes storing a bioreactor and an ETC contained therein within a transport package via an opening in the package, and sealing the opening. Some embodiments are also directed at methods for sterilizing packaging and bioreactors contained therein.

20 Claims, 4 Drawing Sheets

(56) References Cited

U.S. PATENT DOCUMENTS

| | | | | |
|---|---|---|---|---|
| 6,135,304 | A | 10/2000 | Wyslotsky | |
| 6,830,149 | B2 | 12/2004 | Merboth et al. | |
| 2004/0029266 | A1 | 2/2004 | Barbera-Guillem | |
| 2004/0043481 | A1 | 3/2004 | Wilson | |
| 2005/0013726 | A1* | 1/2005 | Hill | A61L 2/208 422/62 |
| 2006/0141623 | A1 | 6/2006 | Smith et al. | |
| 2015/0231628 | A1 | 8/2015 | Nozaki et al. | |
| 2015/0351893 | A1* | 12/2015 | Smith | A61F 2/0095 53/431 |
| 2017/0226462 | A1 | 8/2017 | Wu | |
| 2018/0320122 | A1 | 11/2018 | Blanchard | |
| 2019/0225926 | A1 | 7/2019 | Katou et al. | |

OTHER PUBLICATIONS

International Search report mailed Mar. 11, 2011 for International Application No. PCT/US2020/064598, 10 pages.

Extended European Search Report for European Application No. EP20899029.1 dated Feb. 29, 2024, 12 pages.

* cited by examiner

SYSTEMS, DEVICES AND METHODS FOR ENGINEERED TISSUE CONSTRUCT TRANSPORT AND CONTAINMENT

RELATED APPLICATIONS

This disclosure claims benefit of and priority to U.S. provisional patent application no. 62/946,645, filed Dec. 11, 2019, and entitled, "Systems, Devices and Methods for Engineered Tissue Construct Transport and Containment," the entire disclosure of which is herein incorporated by reference in its entirety.

BACKGROUND

A human acellular vessel (HAV), which may be referred to as an engineered tissue construct or "ETC", made up of human extracellular matrix components (primarily collagen), includes a combination of mechanical and biological properties that mimic native vasculature (or other native tissue) to ensure that the HAV/ETC can withstand physiological pressures (e.g., blood pressure) and promote natural remodeling by the recipient's own cells upon implantation. Additionally, both the HAV/ETC (and similar products) and its primary packaging must be rendered sterile in order to eliminate the opportunity for a local or systemic infection resulting from the surgical procedure.

SUMMARY OF SOME OF THE EMBODIMENTS

Accordingly, in some embodiments of the present disclosure, ETCs are cultivated in a bioreactor (which may also be referred to as a bioreactor bag), that, in some embodiments, is sterilized prior to use. In some embodiments, the bioreactor comprises the "housing" for the ETC throughout not only the manufacturing process, but also storage and shipment, until the bioreactor is finally opened in a surgical theater when the ETC is implanted into a patient. Accordingly, such a procedure maintains an ETC in a sterile condition from cultivation to implantation, eliminating the need for an aseptic transfer or a terminal sterilization. Advantages of this strategy, according to some embodiments, include eliminating the opportunity for microbial agents to contaminate the ETC, and thereby reducing costs associated with clean rooms, aseptic transfer equipment or terminal sterilization, as well as being ideal for process scalability.

In some embodiments, an engineered tissue construct (ETC) transport and containment method is provided and includes storing a bioreactor and an ETC contained therein within a transport package via an opening in the package, and sealing the opening.

Such embodiments, may further include one and/or another of the following (and in some embodiments, at least two of the following, and in some further embodiments, all of the following) features, structure, functionality, or clarification, leading to yet further embodiments of the present disclosure:

- sealing comprises sealing the opening with a sealing membrane;
- the transport package is configured for transporting the bioreactor and ETC contained therein to a surgical theater such that the bioreactor is:
  - removed from the package via unsealing of the opening, and
  - opened to remove the ETC for use in a surgical procedure;

- cultivating the ETC within the bioreactor prior to storing of the bioreactor within the transport package;
- after storing the bioreactor and ETC contained therein within the transport package, sterilizing the package and an interior thereof including the bioreactor stored therein;
- sterilizing comprises exposing the package to a sterilizing medium via a sterilizing means;
- sterilizing comprises exposing the package and the interior thereof, including the bioreactor, to a sterilizing medium via a sterilizing means;
- the sterilizing means comprises an apparatus configured to expose the package and the interior thereof, including the bioreactor, to the sterilizing medium;
- the sterilizing medium comprises a gas or vapor;
- the gas or vapor is selected from the group consisting of: steam, hydrogen peroxide (VHP), and ethylene oxide;
- the sealing membrane includes a plurality of microscopic pores configured to pass gaseous or vaporous molecules of predetermined size out of the interior of the package;
- as a result of sterilizing, the interior of the package and the exterior of the bioreactor are rendered substantially free of active biological material;
- de-cellularization of the ETC prior to storing the bioreactor within the package;
  - wherein in some embodiments, de-cellularization results in at least an interior of the bioreactor and ETC being substantially free from living biological material, and/or prions;
- the sealing membrane comprises a sheet of flashspun high-density polyethylene fibers (e.g., Tyvek® material); and
- storing the package between, e.g., 2-40 degrees Celsius;

In some embodiments, an engineered tissue construct (ETC) transport containment method is provided, which includes optionally cultivating an ETC within an interior of a bioreactor, storing a/the bioreactor and the cultivated ETC contained therein within a transport package via an opening in the package, sealing the opening with a sealing membrane, the membrane including a plurality of pores configured to pass gaseous or vaporous molecules of a predetermined size into and/or out of the interior of the package, exposing the package and an interior thereof, including the bioreactor, to a sterilizing gas or vapor via a sterilizing means, the sterilizing means comprising an apparatus configured to expose the package and the interior thereof, including the bioreactor, to the sterilizing gas or vapor, and storing the package between approximately 2-40 degrees Celsius.

Such embodiments, may further include one and/or another of the following (and in some embodiments, at least two of the following, and in some further embodiments, all of the following) features, structure, functionality, or clarification, leading to yet further embodiments of the present disclosure:

- the package is configured for transporting the bioreactor and ETC contained therein to a surgical theater such that the bioreactor is removed from the package via unsealing of the opening, and opened to remove the ETC for use in a surgical procedure;
- the ETC is cultivated within the bioreactor prior to storing of the bioreactor within the package;
- as a result of sterilizing, at least one of the interior of the package and the exterior of the bioreactor are rendered substantially free of active biological material;

the gas or vapor is selected from the group consisting of: steam, hydrogen peroxide (VHP), and ethylene oxide;

de-cellularization of the ETC prior to storing the bioreactor within the package;

in some embodiments, de-cellularization results in at least one of the interior of the bioreactor and ETC being substantially free from living biological material, and/or prions; and the sealing membrane comprises a sheet of flashspun high-density polyethylene fibers (e.g., Tyvek® material);

In some embodiments, an engineered tissue construct (ETC) transport containment method is provided and comprises storing a bioreactor and an associated cultivated ETC contained therein within a transport package via an opening in the transport package, sealing the opening with a sealing membrane, the membrane including a plurality of pores configured to pass gaseous or vaporous molecules of a predetermined size into and/or out of the interior of the package, placing the sealed transport package in a chamber, providing an airflow to the chamber at an airflow rate, maintaining the chamber at a chamber pressure, optionally dehumidifying the airflow so as to dehumidify the chamber, the dehumidified airflow being provided to the chamber for a dehumidification time, after dehumidification, conditioning the airflow by first injecting a conditioning amount of a sterilizing substance into the airflow for a conditioning time, after first injecting, second injecting of a decontamination amount of the sterilizing substance into the airflow to establish (and in some embodiments, maintain) a decontamination airflow entrained with the sterilizing substance within the chamber, and exposing, within the chamber, the sealed transport package to the decontamination airflow for a decontamination time so as to decontaminate the transport packaging and the bioreactor contained herein.

Such embodiments, may further include one and/or another of the following (and in some embodiments, at least two of the following, and in some further embodiments, all of the following) features, structure, functionality, or clarification, leading to yet further embodiments of the present disclosure:

storing the bioreactor comprises storing each of a plurality of bioreactors an any associated cultivated ETC contained therein within a respective transport package via an opening in the transport package;

placing the sealed transport package in the chamber comprises placing each of the plurality of transport packages in the chamber;

each sealed transport package is exposed to the decontamination airflow for the decontamination time;

exhausting the decontamination airflow from the chamber;

capturing the sterilizing substance contained within the exhausted decontamination airflow;

after the sterilizing substance is captured, upon a concentration of the chamber reaching a safe level, the/each transport package is removed from the chamber;

storing the/each transport package after decontamination;

the/each transport package is stored at a predetermined temperature range;

the temperature range can be between 2 and 40 deg. C;

as a result of the/each transport package being subject to the decontamination airflow, the interior of the transport package and the exterior of the bioreactor are rendered substantially free of active biological material, and/or the/each transport package is configured for transporting a respective bioreactor and an ETC contained therein to a surgical theater such that the bioreactor is removed from the package via unsealing of the opening, and opened to remove the ETC for use in a surgical procedure;

the airflow rate is between 10 and 50 scfm (standard cubic feet per minute), between 20 and 40 scfm, between 25 and 35 scfm, between 29 and 31 scfm, or 30 scfm;

the conditioning amount is between 2.0 g/min and 15 g/min, between 5.0 g/min and 10 g/min, between 7 g/min and 8 g/min, or 7.5 g/min;

the decontamination amount is between 1.0 g/min and 10 g/min, between 2.0 g/min and 5 g/min, between 3 g/min and 4 g/min, or 3.8 g/min;

the chamber pressure is below atmospheric pressure;

the chamber pressure is between −40 Pa and −10 Pa, between −35 Pa and −15 pa, between −30 Pa and −20 Pa, or −25 Pa;

the dehumidification time is between 5 min and 50 min, between 15 min and 40 min, between 20 min and 35 min, or 30 min;

the conditioning time is between 1 min and 10 min, between 2 min and 8 min, between 4 min and 6 min, or 5 min;

the decontamination time is between 30 min and 3 hours, between 1 hour and 2.5 hours, between 2 hours and 2.25 hours, or 2 hours and 5 min; and cultivating the ETC within the bioreactor.

In some embodiments, a system for performing a method according to any one of the methods disclosed herein is provided.

These and other embodiments, advantages and objects thereof will become even more apparent by reference to the detailed description which follows, and corresponding figures, a brief description of which are described below.

BRIEF DESCRIPTION OF THE FIGURES

FIG. 1A: top view;

FIG. 1B: side view;

FIG. 1C: end view;

FIG. 1D: perspective end view;

FIG. 1E: perspective view;

DETAILED DESCRIPTION OF SOME OF THE EMBODIMENTS

Figure 1A:
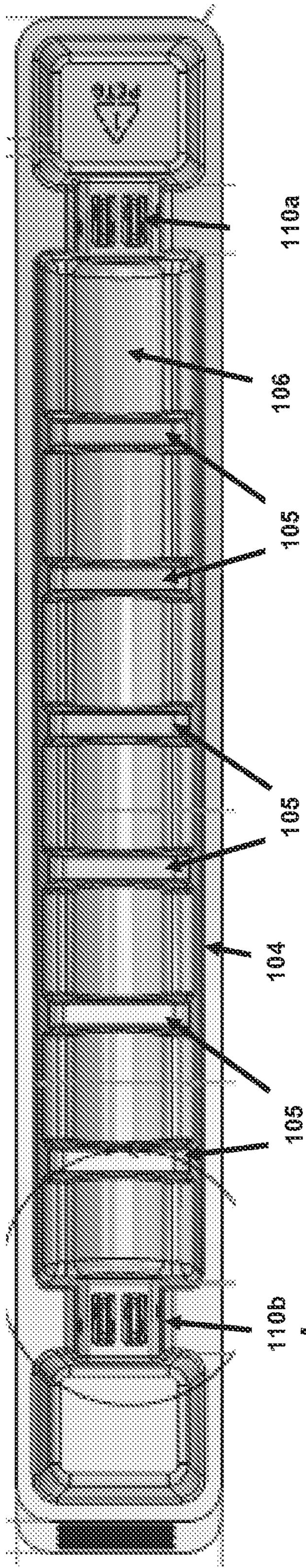
FIGS. 1A-1E illustrate various views of a package (which can also be referred to as a transport package) for containing a bioreactor and its contents, according to some embodiments.
Figure 1B:
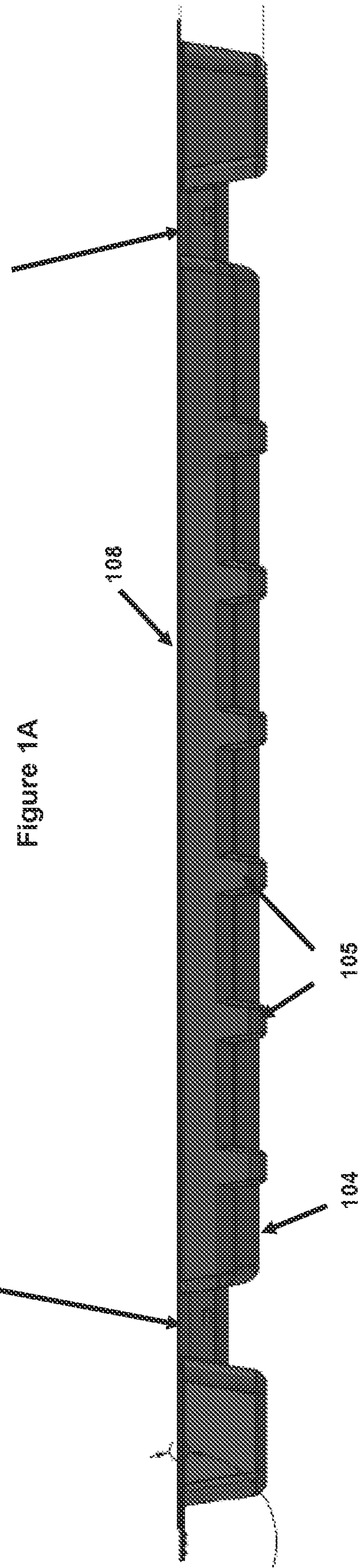
Figure 1C:
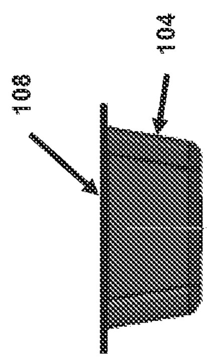
Figure 1D:
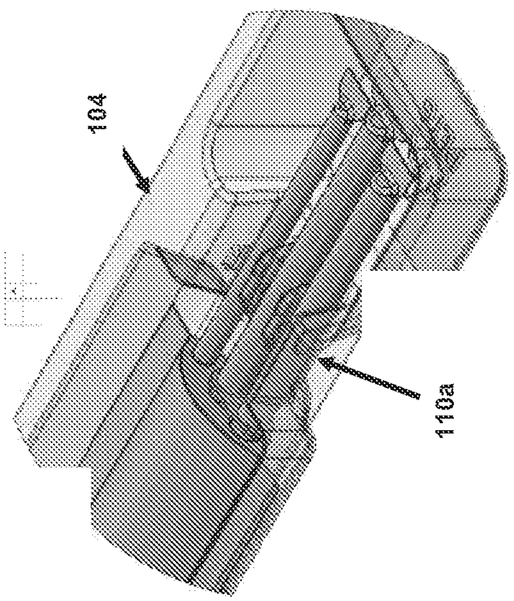
Figure 1E:
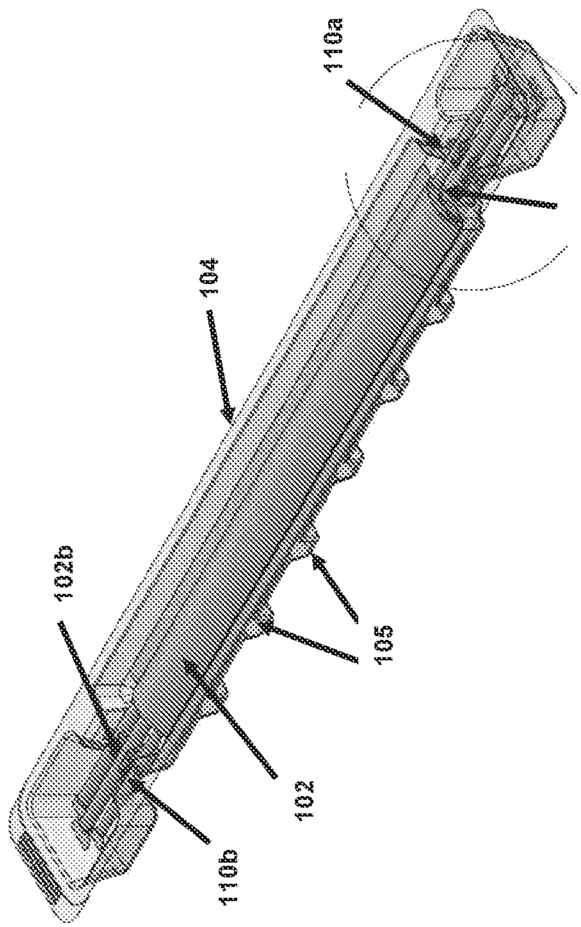

FIGS. 1A-1E illustrate an engineered tissue construct (ETC) transport and containment system and method according to some embodiments. In such embodiments, a bioreactor 102 and an engineered-tissue-construct (ETC) are contained within a transport package 104 via an opening 106 in the package 104 (the ETC, in some embodiments, is cultivated within the bioreactor prior to storing of the bioreactor within the package 104). Thereafter, the opening 106 is sealed with a membrane 108 (see FIGS. 1B-C, "top" of figures) and/or the like. In some embodiments, the sealing membrane can comprise a sheet of flash-spun high-density polyethylene fibers (e.g., Tyvek®). In some embodiments, the Tyvek® material comprises Tyvek® 1073B is used. Such material, in some embodiments, include pores which enable gases and/or vapors to pass (e.g., decontamination substances for decontaminating the package and the interior thereof. The package (which may also be referred to as a transport package), can include various recesses and protrusions, as required, to accommodate the bioreactor structure, or associated tubes and other devices connected or integral with the bioreactor.

In some embodiments, the ETC is de-cellularized prior to storing the bioreactor within the package. Accordingly, such de-cellularization can result in at least an interior of the bioreactor, as well as the ETC being substantially free from living biological organisms and viruses. In some embodiments, de-cellularization can also result in at least an interior of the bioreactor and the ETC being substantially free from prions. De-cellularization can be according to the steps, processes, and timings as specified in U.S. patent publication no. 2008/0248080, herein incorporated by reference in its entirety.

The package 104 is configured for transporting the bioreactor 102 and ETC contained therein to a surgical theater (not shown) such that the bioreactor 102 is removed from the package 104 via unsealing of the opening 106, and opened to remove the bioreactor 102 (and then the ETC from the bioreactor) for use in a surgical procedure.

The package 104 is sized to accommodate both the bioreactor 102 as whole, as well as, in some embodiments, features thereof, including, for example ports, supply tubes, and the like. Moreover, package 104 can include structure 110*a* and 110*b*, that holds up ends 102*a*, 102*b* of the bioreactor, to hold the ends (and/or ports, tubes, and the like) in place during transport. Additionally, package 104 can include one or more, and preferably, a plurality of ribs 105 that can function to at least one of add rigidity to the package 104, and support portions of the bioreactor 102 adjacent thereto.

Figure 2:
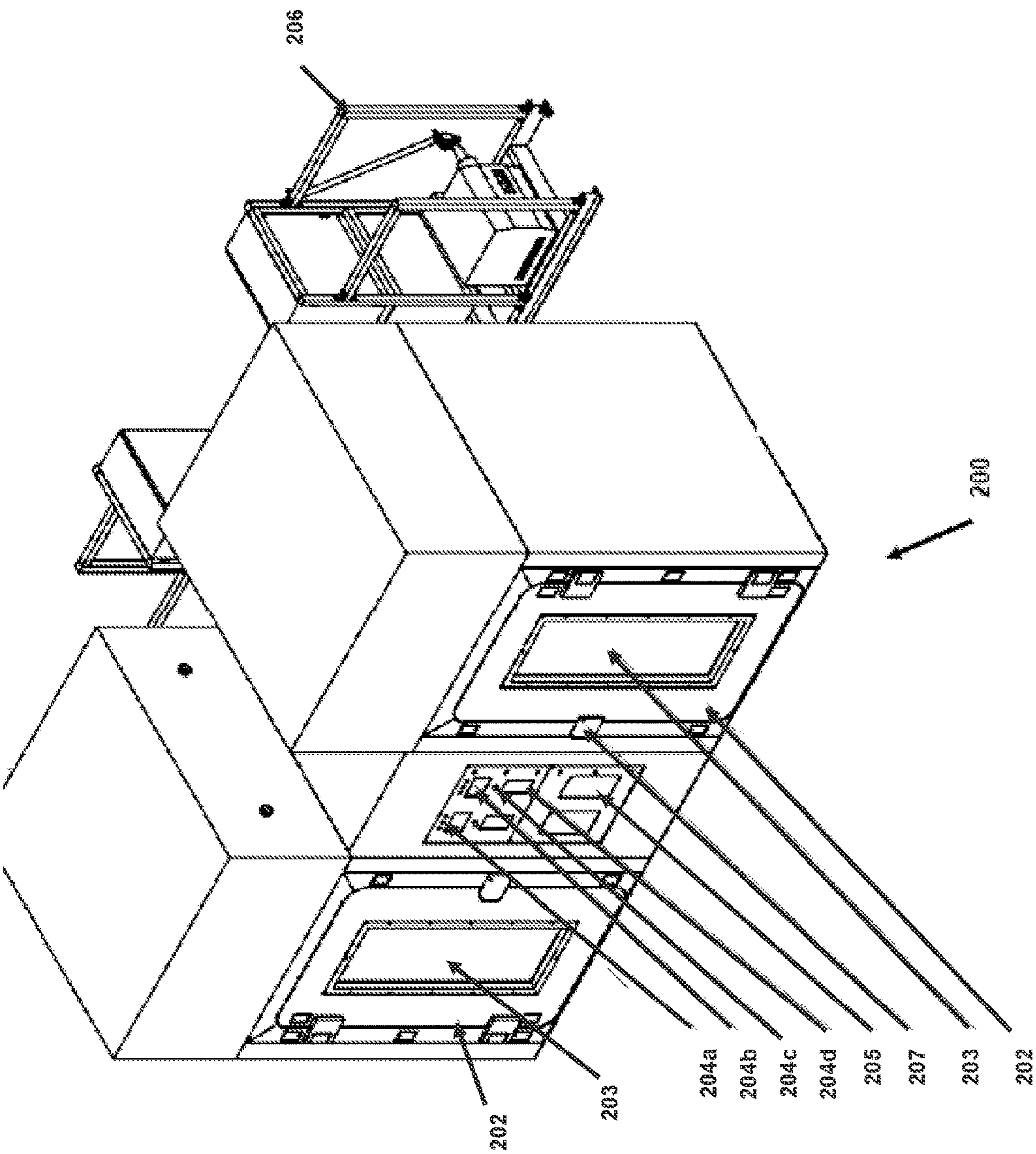
FIG. 2 is a perspective view of a sterilizing means, according to some embodiments of the disclosure.
Figure 3:
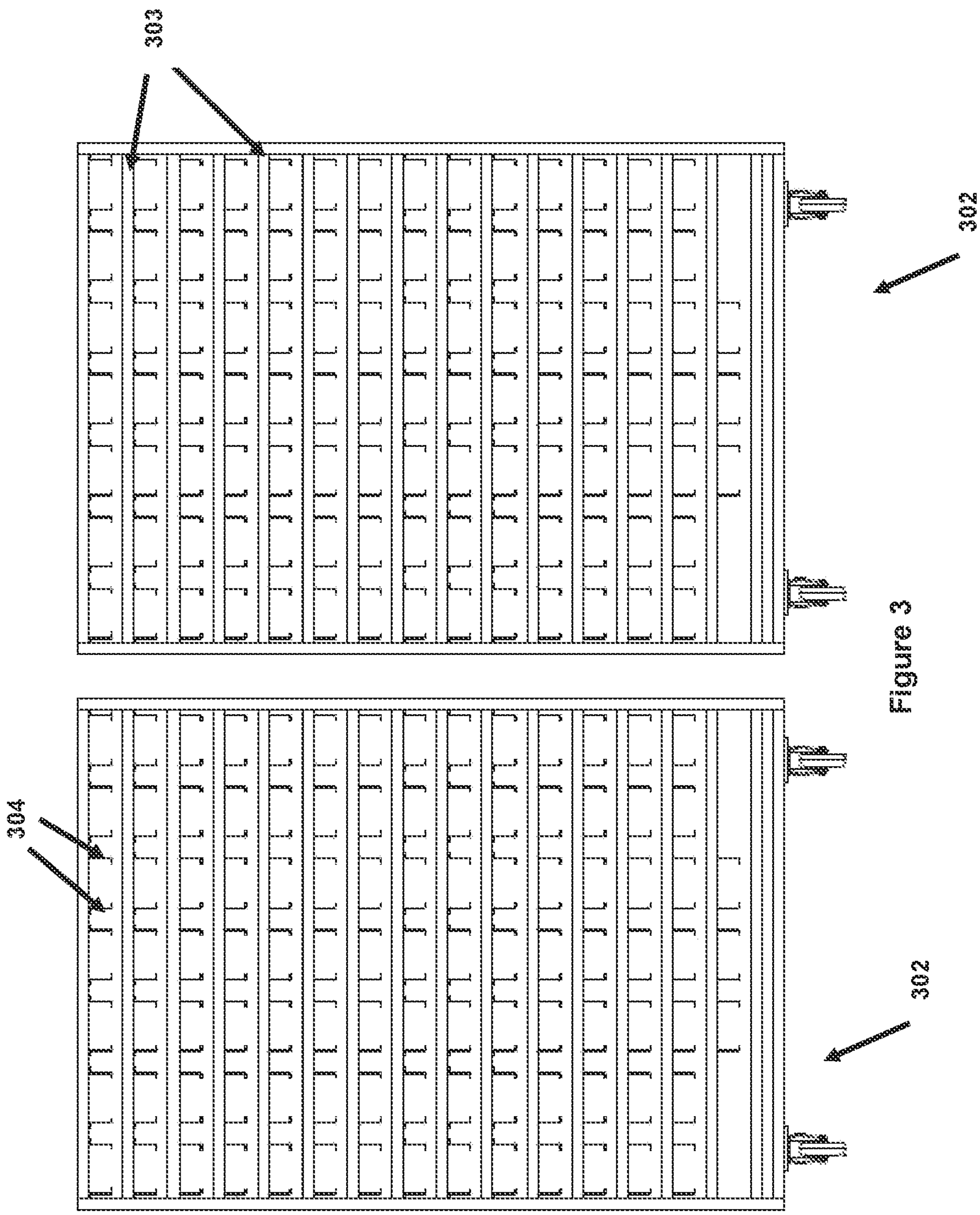
FIG. 3 is a front view of a pair of racking systems for holding a plurality of transport packages; the racking systems for being received by the sterilizing means of FIG. 2.

After placing the bioreactor within the package 104, the package 104 and bioreactor 102 may be sterilized, including, in some embodiments, the interior thereof including the bioreactor 102 stored therein. Sterilizing, in some embodiments, can comprise exposing the package 102 and the interior thereof (in some embodiments, prior to sealing), including the bioreactor, to a sterilizing medium via a sterilizing means, as shown in FIG. 2. The sterilizing means can comprise an apparatus 200 configured to expose the package and the interior thereof, including the bioreactor, to the sterilizing medium. The exposure may be according to a predetermined timing, which can be controlled by the apparatus 200. Apparatus 200, in some embodiments, includes one or more cabinets configured to receive one or more, and preferably a plurality of packages 104 with bioreactors 102 stored therein. In some embodiments, the packages 104 can be placed upon a rack 302, as shown in FIG. 3. Each rack 302 can include rows 303 which include affixing points 304 for each package 104. The sterilizing medium can comprise a gas or vapor, and/or the gas or vapor can be selected from the group consisting of (for example): steam, hydrogen peroxide (VHP), and ethylene oxide.

As shown in FIG. 2, the sterilizing means 200 can be a chambered system/device, including one or more chambers with associated doors 202, and associated controls 204, which can include any one or more of indicator light(s) 204*a*, touch-pad 204*b*, start/stop switches 204*c*, and a printer 204*d*, as well as other items for controlling decontamination processing. The chambered system includes airflow means (e.g., one or more fans), as well as storage 205 for a decontamination substance to inject into the airflow (e.g., "20-liter VHP storage"). The doors to the chamber may include viewing ports 203. Each chamber can be configured such that rack 302 can be easily transported therein (e.g., "wheeled-in"). Each door can be configured for secure and sealed mating with each respective chamber (e.g., gaskets, magnetic interlocking 207, and/or the like). Various electronic and ducting systems associated with the sterilizing means can be provided as an associated system 206 (although one and/or other such features, e.g., fans, ducting, can be provided directly in the chamber system). One or more fans, as noted, can be provided to provide associated one or more airflows (e.g., dehumidifying, decontamination, exhaust, conditioning), and can be set to a percentage of maximum (e.g., "75%" see below chart), for a corresponding, desired airflow rate.

In some embodiments, the process of sterilization includes dehumidification, conditioning, decontamination (with the sterilization medium), and aeration. Such steps may be conducted according to the following timing, for example, according to some embodiments; in some embodiments, the below steps can be done in a range of timings (e.g., within +/−30 15 seconds), although other timings and additional steps may be included, and other processes for sterilization my include different timings of such steps and the elimination of such steps (for example).

10-Log Decontamination Cycle Parameters (to be utilized during routine Production operations)

| | Phase | | | |
|---|---|---|---|---|
| Parameter | Dehumidification | Conditioning | Decontamination | Aeration |
| Time, hh:mm | 00:30 | 00:05 | 02:05 | 01:00 |
| Airflow, SCFM | 30 | 30 | 30 | 30 |
| Injection Rate, g/min | n/a | 7.5 | 3.8 | n/a |
| Humidity, mg/L* | 0.0 | 0.0 | 0.0 | 0.0 |
| Chamber Fan, % | 75 | 75 | 75 | 100 |
| Chamber P, Pa | −25 | −25 | −25 | −25 |

*With a set-point of 0.0 mg/L, a minimum humidity level is not utilized in the cycle control (i.e. 'not used').

The sealing membrane 108 can include a plurality of microscopic pores (not shown) configured to pass gaseous or vaporous molecules of predetermined size of the sterilizing medium into and/or out of the interior of the package. In addition, according to some embodiments, the sealing membrane can be configured to be impermeable to biologics (virus, bacteria, and the like). As a result of sterilizing, the interior of the package and the exterior of the bioreactor are rendered substantially free of active biological material. In some embodiments, the package is stored between approximately 2-40 degrees Celsius until use.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, ranges, and configurations described herein are meant to be an example and that the actual parameters, dimensions, materials, ranges and configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of claims supported by the subject disclosure and equivalents thereto, inventive embodiments may be practiced otherwise than as specifically described and claimed. Inventive embodiments of the present disclosure are directed to each individual feature, step, function, system, article, material, kit, and/or method described herein. In addition, any combination of two or more such features, steps, systems, articles, materials, kits, and/or methods, if such features, systems, articles, materials, steps kits, and methods are not mutually inconsistent, is included within the inventive scope of the present disclosure.

Embodiments disclosed herein may also be combined with one or more features, as well as complete systems, devices and methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. An engineered tissue construct (ETC) transport and containment method comprising:

aseptically cultivating an ETC within a bioreactor;

de-cellularizing the ETC within the bioreactor, the de-cellularized ETC comprising extracellular matrix;

storing the bioreactor within a transport package via an opening in the transport package;

sealing the opening by applying a sealing membrane across the opening, the sealing membrane including a plurality of pores configured to pass gaseous and/or vaporous molecules of a predetermined size into and out of the interior of the transport package via the opening; and performing a sterilization process on the transport package, the sterilization process comprising exposing the interior of the transport package and the exterior of the bioreactor to a sterilizing substance comprising the gaseous and/or vaporous molecules.

2. The method of claim 1, wherein the transport package is configured for transporting the bioreactor to a surgical theater such that the bioreactor is:

removed from the package via unsealing of the opening, and opened to remove the ETC for use in a surgical procedure.

3. The method of claim 1, wherein the sealing membrane comprises a sheet of flashspun high-density polyethylene fibers.

4. The method of claim 1, wherein the de-cellularized ETC is a human acellular vessel.

5. The method of claim 1, further comprising, after performing the sterilization process, storing the transport package at a temperature between 2 degrees Celsius and 40 degrees Celsius.

6. The method of claim 1, wherein storing the bioreactor within the transport package comprises arranging the bioreactor against a plurality of ribs of the transport package, the plurality of ribs configured to support the bioreactor within the transport package.

7. The method of claim 1, wherein sterilizing the interior of the transport package and the exterior of the bioreactor does not sterilize the ETC.

8. The method of claim 1, wherein sterilizing comprises placing the sealed transport package in a chamber and maintaining the chamber at a chamber pressure between −40 Pascals and −10 Pascals.

9. An engineered tissue construct (ETC) transport containment method comprising:

aseptically cultivating an ETC within a bioreactor;

de-cellularizing the ETC within the bioreactor, the de-cellularized ETC comprising extracellular matrix;

storing the bioreactor within a transport package via an opening in the transport package;

sealing the opening by applying a sealing membrane across the opening, the sealing membrane including a plurality of pores configured to pass gaseous and/or vaporous molecules of a predetermined size into and out of the interior of the transport package via the opening;

placing the sealed transport package in a chamber;

performing a sterilization process on the transport package within the chamber, the sterilization process comprising:

providing an airflow to the chamber at an airflow rate;

maintaining the chamber at a chamber pressure below atmospheric pressure;

dehumidifying the airflow so as to dehumidify the chamber, the dehumidified airflow being provided to the chamber for a dehumidification time;

after dehumidification, conditioning the airflow by injecting a conditioning amount of a sterilizing substance comprising the gaseous and/or vaporous molecules into the airflow for a conditioning time;

after injecting the conditioning amount of the sterilizing substance, injecting a decontamination amount of the sterilizing substance into the airflow to establish and/or maintain a decontamination airflow entrained with the sterilizing substance within the chamber; and exposing, within the chamber, the sealed transport package to the decontamination airflow for a decontamination time so as to decontaminate the interior of the transport package and the exterior of the bioreactor contained therein.

10. The method of claim 9, wherein:

storing the bioreactor comprises storing each of a plurality of bioreactors and any associated cultivated ETC contained therein within a respective transport package via an opening in the respective transport package;

placing the sealed transport package in the chamber comprises placing each of the respective transport packages in the chamber; and each sealed transport package is exposed to the decontamination airflow for the decontamination time.

11. The method of claim 10, wherein each sealed transport package is configured for transporting a respective bioreactor to a surgical theater such that the respective bioreactor is removed from each sealed transport package via unsealing of the opening, and wherein the respective bioreactor is opened to remove an ETC therein for use in a surgical procedure.

12. The method of claim 9, wherein the sterilization process further comprises exhausting the decontamination airflow from the chamber and capturing the sterilizing substance contained within the exhausted decontamination airflow.

13. The method of claim 12, wherein after the sterilizing substance is captured, upon a concentration of the chamber reaching a safe level, the sealed transport package is removed from the chamber.

14. The method of claim 9, further comprising storing the sealed transport package at a predetermined temperature range after decontamination.

15. The method of claim 14, wherein the predetermined temperature range of storage of the transport package is between 2 degrees Celsius and 4 degrees Celsius.

16. The method of claim 9, wherein:

as a result of the sealed transport package being exposed to the decontamination airflow, the interior of the sealed transport package and the exterior of the bioreactor are rendered substantially free of active biological material.

17. The method of claim 9, wherein the conditioning amount is between 2.0 g/min and 15 g/min.

18. The method of claim 9, wherein the decontamination amount is between 1.0 g/min and 10 g/min.

19. The method of claim 9, wherein the chamber pressure is between −40 Pascals and −10 Pascals.

20. The method of claim 9, wherein the ETC is not sterilized during the sterilization process.

* * * * *